US006987173B2

(12) United States Patent
Lee et al.

(10) Patent No.: US 6,987,173 B2
(45) Date of Patent: Jan. 17, 2006

(54) PROCESS FOR THE PREPARATION OF ACTIVE SOMATOTROPIN FROM INCLUSION BODIES

(75) Inventors: Yong-Jun Lee, Seoul (KR); Hong-Kyun Lee, Daejeon (KR); Kyuboem Han, Daejeon (KR)

(73) Assignee: LG Chemical Limited, Seoul (KR)

( * ) Notice: Subject to any disclaimer, the term of this patent is extended or adjusted under 35 U.S.C. 154(b) by 726 days.

(21) Appl. No.: 09/811,789

(22) Filed: Jan. 12, 2001

(65) Prior Publication Data

US 2003/0229210 A1 Dec. 11, 2003

Related U.S. Application Data

(63) Continuation of application No. PCT/KR99/00485, filed on Aug. 26, 1999.

(30) Foreign Application Priority Data

Aug. 27, 1998 (KR) ....................... 1998-34910

(51) Int. Cl.
C07K 3/08 (2006.01)

(52) U.S. Cl. ..................... 530/399; 530/311; 530/324; 530/344; 530/824; 530/825; 530/397

(58) Field of Classification Search ................ 530/311, 530/399, 324, 344, 824, 825, 397
See application file for complete search history.

(56) References Cited

U.S. PATENT DOCUMENTS 5,109,117 A * 4/1992 Ho .............................. 530/399

OTHER PUBLICATIONS

Brems, et al., "The Kinetics of Bovine Growth Hormone Folding are Consistent With a Framework Model" The Journal of Biological Chemistry, vol. 262, No. 6: 1987 pp. 2590–2596.

Brems, et al., "Equilibrium Denaturation of Pituitary–and Recombiant–Derived Bovine Growth Hormone" Biochemistry, vol. 24, No. 26; 1985, pp. 7662–7668.

Brems, et al., "Characterization of an Associated Equilibrium Folding Intermediate of Bovine Growth Hormone" Biochemistry, vol. 25, No. 21; 1986, pp. 6539–6543.

Brems, et al., "Helical Formation in Isolated Fragments of Bovine Growth Hormone" Biochemistry, vol. 26, No. 24; 1987, pp. 7774–7778.

Holladay, et al., "Growth Hormone Conformation and Conformational Equilibria" Biochemistry, vol. 13, No. 8; 1974, pp, 1653–1661.

Holzman, et al., "Reoxidation of Reduced Bovine Growth Hormone From a Stable Secondary Structure" Biochemistry, vol. 25, No. 22; 1986, pp. 6907–6917.

Holzman, et al., "pH–Induced Conformational States of Bovine Growth Hormone" Biochemistry, vol. 29, No. 5; 1990, pp. 1255–1261.

* cited by examiner

Primary Examiner—Christopher Tate
Assistant Examiner—Roy Teller
(74) Attorney, Agent, or Firm—Katten Muchin Rosenman LLP

(57) ABSTRACT

A process for the preparation of biologically active somatotropin from inclusion bodies of a recombinant host cell containing an inactive form of said somatotropin protein comprises the steps of:

(a) contacting the inclusion bodies with an aqueous alcohol solution at an alkaline pH to solubilize said protein; and (b) bringing the solubilized protein into contact with a mild oxidizing agent to refold and form intramolecular disulfide bonds between cysteine residues of said protein.

19 Claims, 6 Drawing Sheets ically active somatotropin from inclusion bodies of a recombinant host cell containing somatotropin protein, which comprises solubilizing the inclusion bodies with an aqueous alcohol solution, and refolding and oxidizing the solubilized somatotropin protein to yield active somatotropin.

PROCESS FOR THE PREPARATION OF ACTIVE SOMATOTROPIN FROM INCLUSION BODIES

CROSS REFERENCE TO RELATED APPLICATION

This application is a continuation of International Application No. PCT/KR 99/00485, with an international filing date of Aug. 26, 1999, which designated, the U.S. and is now abandoned.

FIELD OF THE INVENTION

The present invention relates to a process for the preparation of somatotropin from inclusion bodies. More specifically, it pertains to a process for preparing biologically active somatotropin from inclusion bodies of a recombinant host cell containing somatotropin protein, which comprises solubilizing the inclusion bodies with an aqueous alcohol solution, and refolding and oxidizing the solubilized somatotropin protein to yield active somatotropin.

BACKGROUND OF THE INVENTION

Heterologous proteins expressed in transformed host cells occur either in a soluble form or in the form of inactive and insoluble inclusion bodies(or refractile bodies) depending on such factors as redox environment of the host cell, the expression level and the nature of the protein. There also exists a borderline case wherein both soluble and insoluble forms of proteins are expressed simultaneously. The proteins expressed in the form of inclusion bodies must be solubilized and renaturized to obtain biologically active proteins and there have been developed several methods for the renaturization of proteins produced in the form of inclusion bodies.

A common method utilizes a high concentration of denaturing chaotropic agents, e.g., urea and guanidine salts, in solubilizing inclusion bodies and the solubilized proteins are renatured after diluting or ultrafiltering the solution to lower the concentration of the denaturing agent. In this method, the solubilizing process is carried out at a high concentration, e.g., 5 to 9 M, of the denaturing agent and the renaturing process, at a lower concentration, e.g, 1 to 5 M(see, e.g., European Patent No. 0 114 506). Further, it has been reported that the addition of a small amount of an alcohol to the solution containing the denaturing agent enhances the solubilization and refolding rates(see, U.S. Pat. No. 5,109,117).

A second method carries out the solubilization of inclusion bodies at a high pH, wherein a protein is denatured, by adding an alkali such as NaOH to a solubilizing solution, and renaturing the protein by lowering the pH(see, e.g., Korean Patent No. 86911). This method may be effectively combined with the above mentioned common method to loosen the strong non-covalent attractions between the proteins in inclusion bodies.

A third method employs a *surfactant for the solubilization of inclusion bodies(see, e.g., U.S. Pat. No. 5,023,323). The hydrophobic portion of the surfactant dissipates the attractive force between proteins in the inclusion bodies by interacting strongly with the proteins, while the hydrophilic portion thereof gets in close contact with water. Thus, a surfactant solubilizes the inclusion bodies by attaching itself to protein monomers in an aqueous solution to form a stable structure. However, this method has the problem that it is difficult to remove the strongly interacting surfactant from renatured proteins.

Protein inclusion bodies which have isoelectric points generally at around neutral pH are formed when protein monomers having no net charge aggregate at a neutral pH due to strong non-covalent attractions therebetween. A denaturing agent when present at a high concentration offsets the non-covalent attractions, thereby solubilizing the inclusion bodies. Further, at a highly alkaline pH, amino acid residues of proteins become charged, thereby further facilitating solubilization of the inclusion bodies.

When a protein having cysteine residues is placed at a sufficiently high pH for the dissociation of the free SH groups of the cysteine residues, oxidation by a mild oxidant such as air occurs slowly to form intramolecular disulfide bonds between the cysteine groups. However, undesirable intermolecular disulfide bonds may also form between two or more protein monomers resulting in the formation of protein dimers, trimers and other polymeric forms.

In fact, the known methods for the renaturation of somatotropin are hampered by the problem that the proportion of the dimeric and polymeric forms of somatotropin is relatively high and, accordingly, there exists a need to develop an effective method to produce biologically active somatotropin at a high yield while minimizing the formation of the dimeric and polymeric forms of somatotropin. As it is difficult to remove the inactive dimeric and polymeric forms of somatotropin in a purification process, it is important to suppress the formation thereof in the refolding and reoxidation process. The present inventors have unexpectedly discovered that the use of a concentrated alcohol solution containing no chaotropic agents, particularly an aqueous isopropyl alcohol or n-propyl alcohol solution in the solubilizing process significantly reduces the formation of the dimeric and polymeric forms of somatotropin.

SUMMARY OF THE INVENTION

Accordingly, it is a primary object of the present invention to provide an improved process for renaturing somatotropin.

In accordance with the present invention, there is provided a process for the preparation of biologically active somatotropin from inclusion bodies of a recombinant host cell containing an inactive form of said somatotropin protein, which comprises the steps of:

(a) contacting the inclusion bodies with an aqueous alcohol solution at an alkaline pH to solubilize said protein; and (b) bringing the solubilized protein into contact with a mild oxidizing agent to refold and form intramolecular disulfide bonds between cysteine residues of said protein.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1:
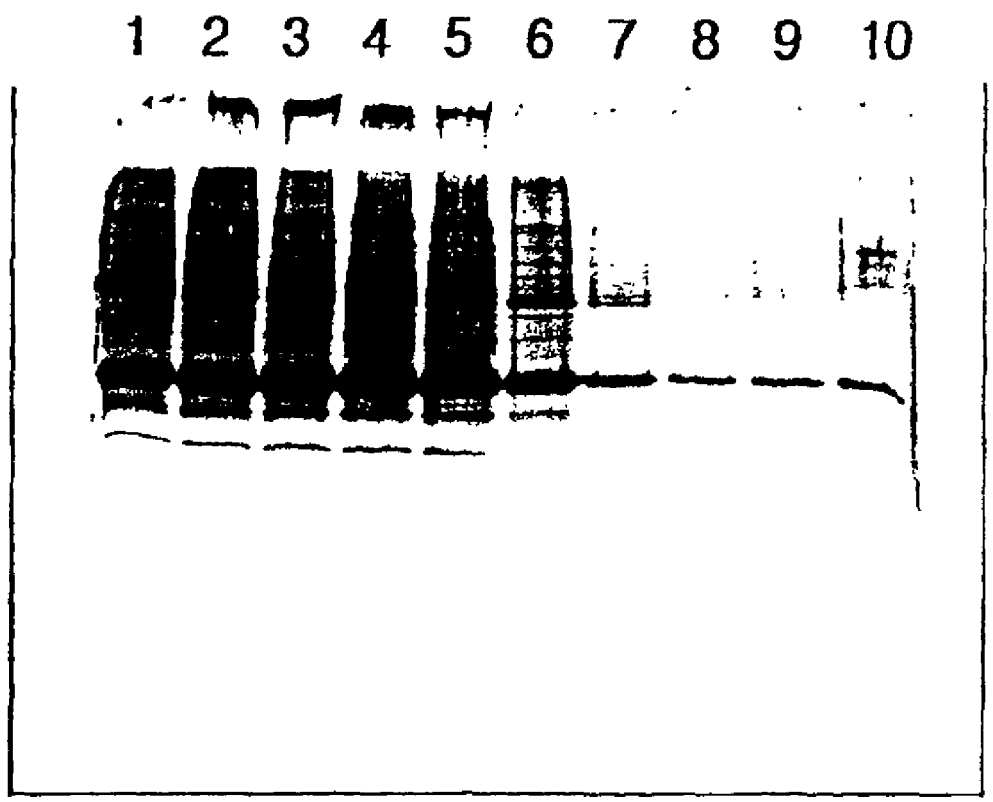
FIG. 1 shows the correlation between the n-propyl alcohol concentration in the solubilizing step and the solubility of somatotropin as determined by reducing SDS-PAGE.

As used herein, the following terms shall have the meanings as described below:

The term "somatotropin" refers to mammalian, avian or fish proteinaceous growth hormones. It may include, but may not be limited to, human, bovine, porcine, horse, goat, ovine, canine, feline, chicken, flatfish, rockfish, salmon or eel somatotropin. Further, it may also include the somatotropin analogues in which amino acid residues are either deleted from, added to or different than the amino acid sequences of the naturally occurring somatotropins, provided that the analogues maintain the bioactivities of the naturally occurring ones. For instance, the present invention may be employed for the naturation of bovine somatotropin (BST) and porcine somatotropin(PST) analogues inclusive of ala-BST, met-BST, ala-PST and met-PST. It is well-known in the field of protein purification that the proteins having analogous physicochemical properties may be purified in accordance with a substantially same procedure, and, accordingly, the present invention also includes the purification of analogous proteins of somatotropin.

The term "inclusion bodies" refers to cytoplasmic aggregates containing heterologous proteins expressed in a transformed host cell, which can be recovered by separating from the cytoplasm. These aggregates appear as bright spots under a microscope.

The term "transformed host cell" refers to a microbial cell which contains a heterologous gene for expressing a somatotropin. Exemplary host cells include procaryotic cells such as an $E.\ coli$ cell, as well as eucaryotic cells such as a yeast cell.

The term "solubilization" refers to the dissociation of inclusion bodies into unit protein molecules by a suitable treatment. The suspension containing the inclusion bodies becomes clear as the solubilization progresses.

The term "refolding" refers to the folding of the dissociated protein molecules produced in the solubilizing process into their native three-dimensional conformation. This procedure is affected by the amino acid sequence of the protein. It is well-known that the disulfide bonds are formed in correct positions when the refolding precedes the formation of disulfide bonds in a protein, thereby causing the formation of an active protein of native conformation.

The term "reoxidation" refers to the formation of the intramolecular disulfide bonds between the cysteine residues of the refolded protein molecules through an oxidation reaction. As the redox potential in an $E.\ coli$ cell is high, the cysteine residues of somatotropin exist as a reduced state, and, accordingly, a stable somatotropin molecule may be formed only when the reoxidation process is carried out subsequently to the solubilizing process for the stabilization of the three dimensional structure.

The present invention employs a high concentration of a water-soluble alcohol, preferably, isopropyl alcohol or n-propyl alcohol, for solubilizing the somatotropin produced in the form of inclusion bodies. Such alcohols are believed to change the polarity of water to weaken the non-covalent attraction in the inclusion bodies, and to offset the non-covalent attractions between the protein molecules. If the pH of the solution in the solubilizing process increases to a highly alkaline value, the amino acid residues of the protein become charged to further weaken the non-covalent attraction between the proteins.

Then, the solubilized somatotropin is contacted with a mild oxidizing agent, e.g., oxygen or hydrogen peroxide, in the presence of the alcohol used in the solubilizing process, preferably, at a lower concentration than that used in the solubilizing process, to prepare active somatotropin through the refolding/reoxidation process.

The overall process for purifying somatotropin from a recombinant $E.\ coli$ cell by employing the present invention may be illustrated as follows.

Inclusion bodies containing somatotropin may be recovered by any conventional method, e.g., that described in Korean Patent No. 86911. Specifically, $E.\ coli$ cells expressing somatotropin are disrupted with a homogenizer in a cell disrupting buffer containing a non-ionic surfactant and insoluble inclusion bodies are recovered using a centrifuge. The recovered inclusion bodies are washed with a buffer containing a non-ionic surfactant and ethylene diamine tetraacetic acid(EDTA) and, subsequently with water to remove the impurities.

The washed inclusion bodies are suspended in an aqueous alcohol solution, preferably a 10 to 50% (v/v) isopropyl alcohol or n-propyl alcohol solution, more preferably, a 20 to 40% isopropyl alcohol solution, to a concentration of 1 to 10 g/l. The suspension is kept at a temperature ranging from 0 to 50° C., preferably 30 to 50° C., more preferably 35 to 40° C. and a pH above 9, preferably, 12 to 13, and then allowed to stand for a time period ranging from 5 to 30 min. to dissolve the inclusion bodies.

Subsequently, the resulting solution is diluted with water or subjected to ultrafiltration to lower the alcohol concentration to 1 to 35%, preferably, 10 to 20%, when the alcohol is isopropyl alcohol or n-propyl alcohol. Then, the solution is exposed to air and gently stirred for 1 to 8 hours to refold and effectuate the oxidative formation of intramolecular disulfide bonds between cysteine residues of the somatotropin protein, thereby producing active somatotropin. The refolding/reoxidation reaction is carried out at a temperature ranging from 0 to 50° C., preferably, 5 to 40° C., more preferably, 10 to 20° C., and a pH above 8.4, preferably, from 12 to 13. At this time, a metal catalyst, e.g., $CuCl_2$, $MgSO_4$ and $CaSO_4$, may be added to the reaction mixture for promoting the reaction. Further, the refolding/reoxidation reaction may also be carried out after removing isopropyl alcohol or n-propyl alcohol.

In the present invention, a reducing agent may be added to the reaction mixture in the solubilizing process, refolding/reoxidation process or both of them for the purpose of enhancing the rate of the formation of correct disulfide bonds. In case of the solubilizing process, 0.0001 to 0.5% of 2-mercaptoethanol or a correspondingly effective amount of other reducing agent, e.g., cysteamine, glutathione, cysteine and a redox mixture thereof, may be employed and it is preferred to employ 0.001 to 0.05% (v/v) of 2-mercaptoethanol. In case of the refolding/reoxidation process, 0 to 0.25% of 2-mercaptoethanol or a correspondingly effective amount of other reducing agents exemplified above may be preferably employed.

Upon the completion of the somatotropin renaturation, the activated somatotropin may be further purified according to a conventional method, e.g., that of Korean Patent No. 86911 which includes ultrafiltration and anion exchange chromatography, to obtain pure somatotropin at a high yield.

The inventive renaturation process is advantageous in that it is possible to obtain an active somatotropin at a high yield from the inclusion bodies produced in a recombinant host cell, without employing a denaturing agent, e.g., urea, or a surfactant, e.g., sodium dodecyl sulfate(SDS) which is conventionally employed.

The following Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

Effect of Adding n-Propyl Alcohol in the Solubilizing process (Step 1) Recovery of Inclusion Bodies Recombinant *E. coli* cells expressing bovine somatotropin (KFCC-10693; Deposited: on May 25, 1990 with the Korean Federation of Culture Collection(Address: College of Engineering, Yonsei University, Sodaemun-Gu, Seoul 120–749, Republic of Korea)) were cultured in a 450 l fermenter and a 300 l aliquot thereof was adjusted to pH 4.8 by the addition of acetic acid. The resulting solution was centrifuged with a continuous centrifuge(BTPX 2150, Alpha-Laval) to recover an *E. coli* cell slurry. The slurry was suspended in distilled water to a final volume of 200 l with the addition of 0.1% Triton X-100 and 10 mM EDTA. The suspension was passed twice through a high pressure homogenizer(SHL 15, Alpha-Laval) at 14,000 psi and a flow rate of 200 l/h to disrupt the cells, and the resulting homogenate was subjected to continuous centrifugation to obtain a slurry containing the inclusion bodies. The slurry was suspended in 120 l of an aqueous solution containing 0.625% Triton X-100 and 50 mM EDTA. The suspension was stirred vigorously with polytron(PT 10/35, KINEMATICA GmBH) for 30 min., diluted with distilled water to 240 l and centrifuged to obtain precipitates. The precipitates were suspended in 180 l of distilled water, stirred vigorously with polytron(PT 10/35, KINEMATICA GmBH) for 15 min., and centrifuged to obtain inclusion bodies as precipitates. The precipitates were suspended in 100 l of distilled water.

(Step 2) Solubilization of Inclusion Bodies and Refolding/Reoxidation of Bovine Somatotropin To each of five 350 ml portions of the inclusion body suspension obtained in Step 1 was added 100, 200, 300, 400 or 500 ml of n-propyl alcohol and distilled water was added thereto to a volume of 1 l. The n-propyl alcohol concentrations of these suspensions corresponded to 10, 20, 30, 40 and 50% (v/v), respectively. The temperature of each suspension was adjusted to 37° C., an aqueous NaOH solution was added thereto with gentle stirring to a pH ranging from 12 to 13, and then allowed to stand for 10 min. to completely dissolve the inclusion bodies.

The resulting solubilized solution was diluted with distilled water to 2 l, gently stirred under air at room temperature for 2 hours, and centrifuged. The resulting supernatant and pellets were analyzed with reducing SDS-PAGE to determine the somatotropin contents. The result is shown in FIG. 1, wherein Lanes 1 to 5 represent respectively to the supernatants obtained by employing 10, 20, 30, 40 and 50 % (v/v) of n-propyl alcohol in the solubilizing process; and Lanes 6 to 10, the corresponding precipitates. As can be seen in FIG. 1, the amount of undissolved somatotropin remaining in the precipitates starts to decrease at Lane 7(20%(v/v) of n-propyl alcohol) and remains nearly constant at a low level at Lanes 8(30% n-propyl alcohol) to 10(50% n-propyl alcohol). This result shows that somatotropin is effectively solubilized in an aqueous solution containing 20% or more of n-propyl alcohol.

EXAMPLE 2

Effect of Adding Isopropyl Alcohol in the Solubilizing Process

Figure 2:
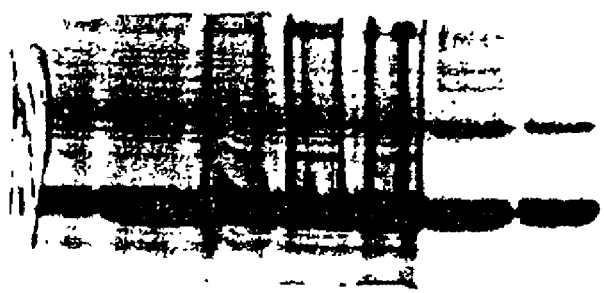
FIG. 2 illustrates the correlation between the isopropyl alcohol concentration in the solubilizing step and the solubility of somatotropin as determined by reducing SDS-PAGE.

In order to investigate the effect of isopropyl alcohol addition on the solubilization of somatotropin, the procedure of Example 1 was repeated except that isopropyl alcohol was employed in the solubilizing process in place of n-propyl alcohol. FIG. 2 shows the result of reducing SDS-PAGE, wherein Lanes 1 to 5 corresponds respectively to the supernatants obtained by employing 10, 20, 30, 40 and 50% (v/v) of isopropyl alcohol in the solubilizing process; and Lanes 6 to 10, the corresponding precipitates. As can be seen in FIG. 2, the amount of undissolved somatotropin remaining in the precipitates is significantly low at Lane 8(30% (v/v) of isopropyl alcohol) and remains nearly constant at a low level at Lanes 9(40% isopropyl alcohol) and 10(50% isopropyl alcohol).

EXAMPLE 3

Figure 3:
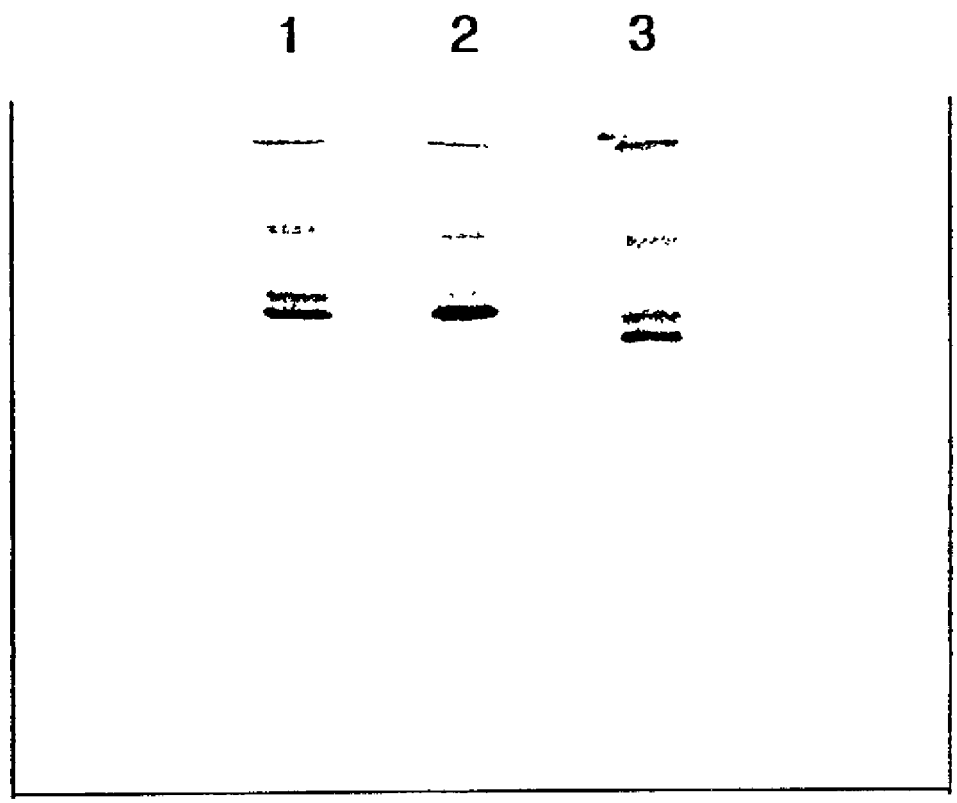
FIG. 3 discloses the correlation between the isopropyl alcohol concentration in the refolding/reoxidation step and the somatotropin renaturation rate as determined by non-reducing SDS-PAGE.

Effect of Varying Isopropyl Alcohol Concentration in the Refolding/Reoxidation Process In order to investigate the effect of varying the isopropyl alcohol concentration on the renaturation of somatotropin, the procedure of Example 1 was repeated except that 350 ml (35%) of isopropyl alcohol was added in the solubilizing process. The solubilized solution thus obtained was used as is in the refolding/reoxidation process, or diluted with distilled water to a final volume of 2 l or 4 l before being subjected to the refolding/reoxidation process. As can be seen from the result of non-reducing SDS-PAGE shown in FIG. 3, the amount of renatured somatotropin is higher when the solubilized solution was diluted 2-fold(Lane 2) than the undiluted case(Lane 1) or when it was diluted 4-fold(Lane 3).

EXAMPLE 4

Temperature Effect in the Solubilizing Process

Figure 4:
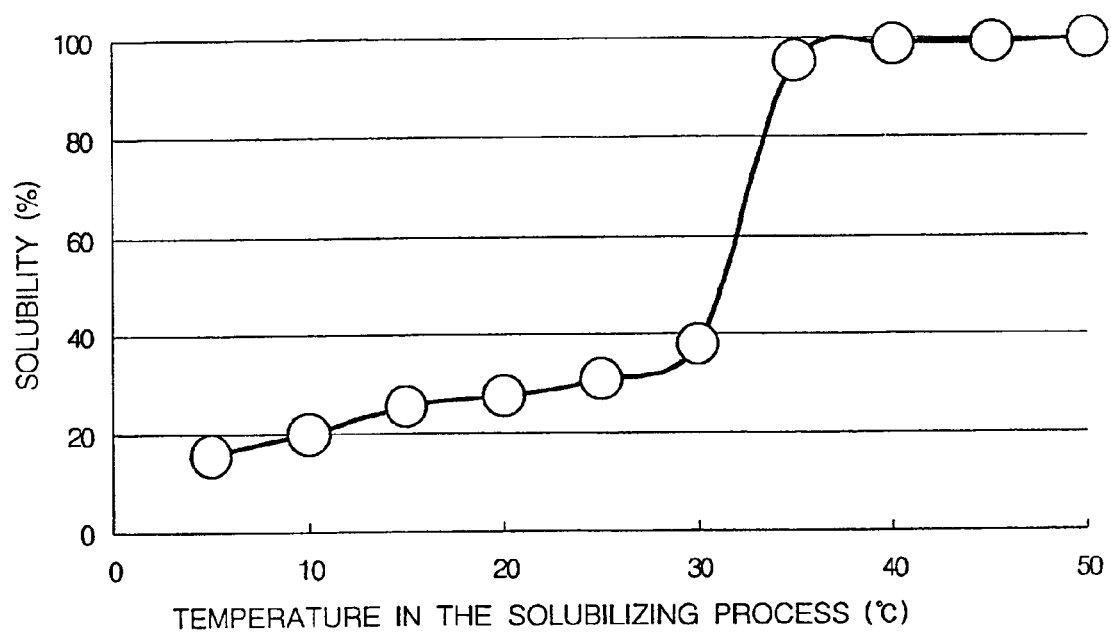
FIG. 4 depicts the change in the solubility of somatotropin as function of temperature in the solubilizing step as determined by reducing SDS-PAGE.

In order to investigate the effect of varying temperature on the solubilization of somatotropin, the procedure of Example 1 was repeated except that 350 ml (35%) of isopropyl alcohol was added and the temperature was varied from 5, 10, 15, 20, 25, 30, 35, 40, 45 to 50° C. in the solubilizing process. The solubility(%) of somatotropin was determined with reducing SDS-PAGE and the result is shown in FIG. 4. As shown in FIG. 4, a maximum rate was observed at above 30° C.

EXAMPLE 5

Figure 5:
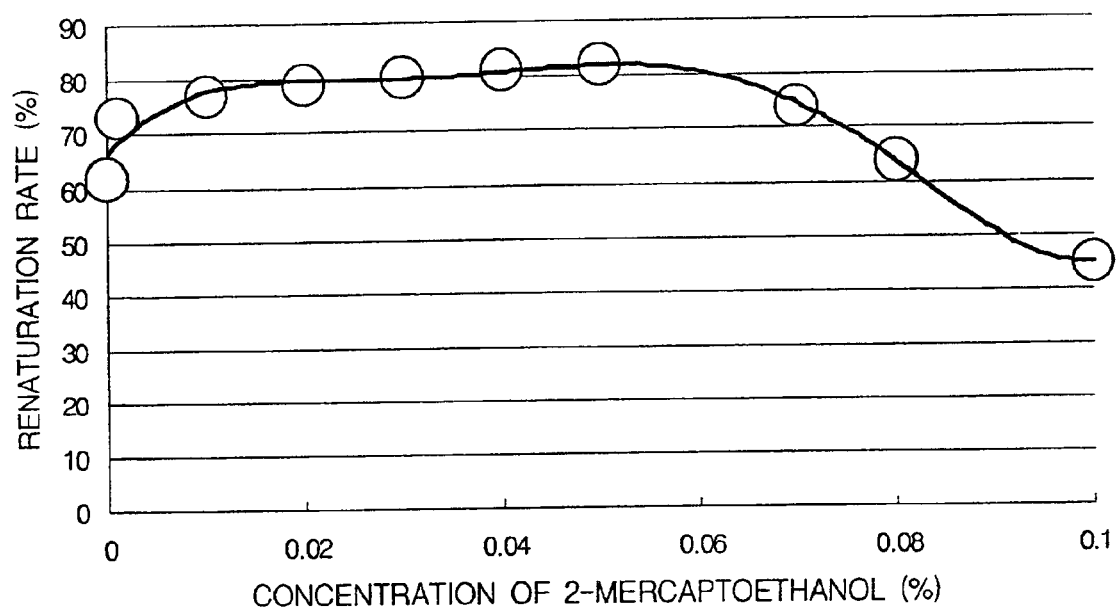
FIG. 5 displays the somatotropin renaturation rate as function of the 2-mercaptoethanol concentration in the refolding/reoxidation step as determined by reducing/non-reducing SDS-PAGE.

Effect of Adding a Reducing Agent (2-Mercaptoethanol) in the Refolding/Reoxidation Process In order to investigate the effect of adding 2-mercaptoethanol on the refolding and reoxidation of somatotropin, the procedure of Example 1 was repeated except that 350 ml(35%) of isopropyl alcohol was added in the solubilizing process, and 2-mercaptoethanol was added as a reducing agent at a concentration of 0, 0.001, 0.01, 0.02, 0.03, 0.04, 0.05, 0.07, 0.08 or 0.1% in the solubilizing process. Renaturation rate(%) of somatotropin was determined with reducing/non-reducing SDS-PAGE and the result in FIG. 5 show that the renaturation rates are 62, 73, 77, 79, 80, 81, 82, 74, 64 and 45%, respectively.

EXAMPLE 6

Effect of Adding a Reducing Agent (Cysteamine) in the Refolding/Reoxidation Process In order to investigate the effect of adding cysteamine on the refolding and reoxidation of somatotropin, the procedure of Example 1 was repeated except that 350 ml (35%) of isopropyl alcohol was added in the solubilizing process, 5 mM of cysteamine was added as a reducing agent in the refolding/reoxidation process, and the reaction mixture was stirred for 6 hours. The renaturation rate(%) of somatotropin determined with reducing/non-reducing SDS-PAGE was 78%.

EXAMPLE 7

Figure 6:
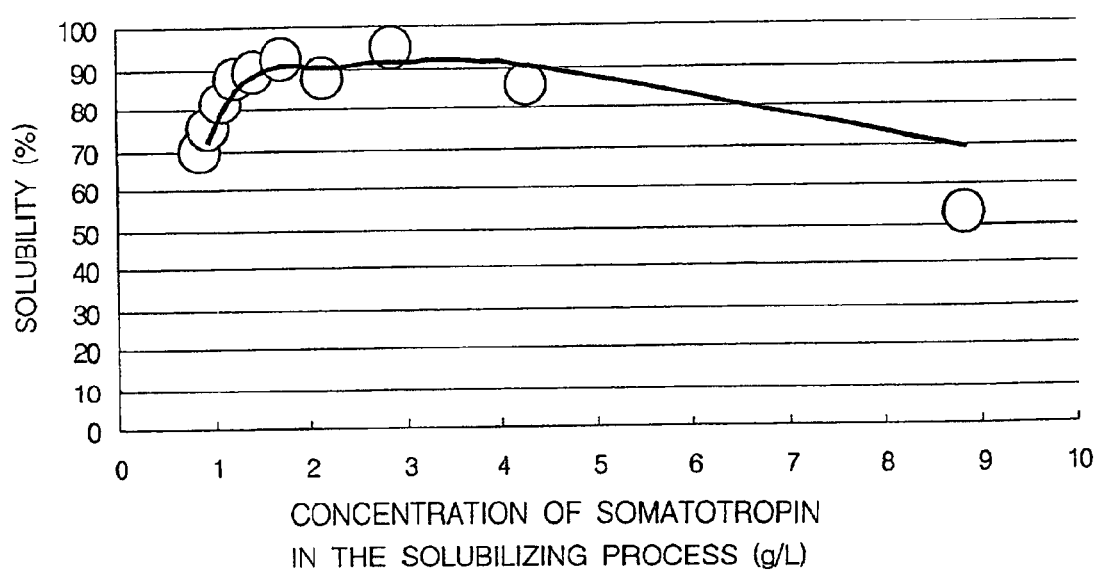
FIG. 6 presents the solubility of somatotropin as function of the somatotropin concentration in the solubilizing step as determined by reducing/non-reducing SDS-PAGE.

Effect of Varying the Somatotropin Concentration in the Solubilizing Process In order to investigate the effect of varying the somatotropin concentration on its solubilization, the procedure of Example 1 was repeated except that 350 ml (35%) of isopropyl alcohol was added and the concentration of bovine somatotropin in the inclusion body suspension was adjusted to 0.85, 0.95, 1.0, 1.2, 1.4, 1.7, 2.1, 2.9, 4.3 or 8.8 g/l in the solubilizing process. The solubility(%) of somatotropin was determined by reducing SDS-PAGE(quantification and comparison of the amounts of somatotropin in the supernatant and precipitates) and the result in FIG. 6 shows that the extent of solubilization varying from 70, 75, 82, 88, 89, 92, 88, 95, 86 to 53% is accordance with the change in the somatotropin concentration as above.

EXAMPLE 8

Purification of Bovine Somatotropin Expressed in E. coli (Step 1) Recovery of the Inclusion Bodies Recombinant E. coli cells expressing bovine somatotropin (KCTC 0644BP; Deposited on Jul. 2, 1999 with the Korean Collection for Type Cultures(Address: Korea Research Institute of Bioscience and Biotechnology, #52, Oun-dong, Yusong-ku, Taejon 305–333, Republic of Korea) under the terms of the Budapest Treaty on the International Recognition of the Deposit of Microorganism for the Purpose of Patent Procedure) were subjected to a fed batch culture in a 10 l fermenter and the pH of the resulting culture was adjusted to 4.8 by the addition of acetic acid.

The culture("Cell F") was centrifuged with a continuous centrifuge(BTPX 2150, Alpha-Laval) to recover the E. coli cell pellets. The pellets were suspended in distilled water to a final volume of 4 l with the addition of 0.1% Triton X-100 and 10 mM EDTA. The suspension("Cell S") was passed twice through a microfluidizer(Microfluidics corporations) at 8,000 psi to disrupt the cells, and the resulting homogenate("Cell H") obtained in a yield of 91.2% from Cell F was subjected to a continuous centrifugation to obtain precipitates containing the inclusion bodies. The precipitates were suspended in 10 l of an aqueous solution containing 0.625% Triton X-100 and 50 mM EDTA. The suspension was stirred vigorously with a polytron(PT 10/35, KINEMATICA GmBH) for 30 min., diluted with distilled water to 5 l and centrifuged to obtain precipitates in a yield of 47.2% based on the weight of Cell H. The precipitates were diluted with distilled water to 2 l, and the resulting suspension ("TEW") was stirred vigorously with a polytron for 15 min. and centrifuged(high speed centrifuge J2-21M, BECKMAN) to obtain precipitates in a yield of 81.4% based on TEW. The precipitates were suspended in distilled water to 0.5 l, and the resulting suspension("WFIW-1") was stirred and centrifuged as above to obtain precipitates in a yield of 89.6% based on WFIW-1. The precipitates were suspended in distilled water to 0.5 l.

(Step 2) Solubilization of Inclusion Bodies and Refolding/Reoxidation of Bovine Somatotropin Added to 250 ml of the suspension of inclusion bodies ("WFIW-2") obtained in Step 1 were 350 ml(35%) of isopropyl alcohol and 0.02% of 2-mercaptoethanol, and the mixture was adjusted to 1 l by the addition of distilled water. The concentration of bovine somatotropin in the resulting suspension was about 2.5 g/l. The suspension was warmed to 37° C. and its pH was adjusted to 12–13 with the addition of an aqueous NaOH solution with gentle stirring, and then allowed to stand for 10 min. to completely dissolve the inclusion bodies. The resulting solution was diluted with distilled water to 2 l, and gently stirred under air at room temperature for 2 hours.

(Step 3) Purification of Bovine Somatotropin

The solution of inclusion bodies obtained in Step 2 was centrifuged to remove insoluble impurities and the supernatant was subjected to ultrafiltration to obtain a filtrate containing materials having a molecular weight below 300,000 daltons. The filtrate was subjected to ultrafiltration to obtain a retentate containing substances having a molecular weight higher than 10,000 daltons. The retentate was diluted with water for injection (WFI) and then passed through an ultrafiltration membrane (Molecular weight cut-off: 10,000 daltons) to obtain a concentrate. This dilution and concentration process was repeated four times and the concentrate was diluted with distilled water to obtain a solution having a conductivity of 800 micro-mho and pH 9.0. Contained in this solution was somatotropin in a yield of nearly 100% based on the amount of somatotropin in WFIW-2. 2 l of the resulting solution("LS") was adsorbed on a DEAE-sepharose column(Pharmacia Biotech), which was previously equilibrated with 10 mM glycine buffer, at a flow rate of 20 l/hour and washed sufficiently with 10 mM glycine buffer. The adsorbed material was eluted with a glycine buffer containing 90 mM NaCl to obtain fractions containing bovine somatotropin("DEAE"). The overall yield of finally purified bovine somatotropin was nearly 28.5% based on the amount of somatotropin in Cell F.

COMPARATIVE EXAMPLE 1

Renaturation of Bovine Somatotropin Employing a Denaturing Agent(Urea)

Renaturation of bovine somatotropin is conducted in accordance with the Holzman method(T. F. Holzman et al., Biochemistry, 25, 6907–6917(1986)). Specifically, 250 ml of the inclusion body suspension obtained in Step 1 of Example 8 was diluted with distilled water to a final volume of 1.3 l with the addition of urea to a concentration of 4.5 M. The resulting solution was adjusted to pH 10.5 by the addition of an aqueous NaOH solution and stirred at room temperature for 8 hours. Bovine somatotropin was purified from the resulting solution in accordance with the method of Step 3 of Example 8.

The renaturation yield(%) of bovine somatotropin in urea refolding step was 83.7% based on the amount of somatotropin in WFIW-2 and overall purification yield was 20.4% based on the amount of somatotropin in Cell F.

EXAMPLE 8

Purification of Porcine Somatotropin Expressed in *E. coli*

Inclusion bodies containing porcine somatotropin were recovered in accordance with the method of Step 1 of Example 8 from the recombinant *E. coli* cells expressing porcine somatotropin(KCTC 0523BP; Deposited on Sep. 24, 1998 with the Korea Research Institute of Bioscience and Biotechnology Korean Collection for Type Cultures (Address: KCTC, KRIBB, #52, Oun-dong, Yusong-ku, Taejon 305–333, Republic of Korea) under the terms of the Budapest Treaty on the International Recognition of the Deposit of Microorganism for the Purpose of Patent Procedure), and the procedures of Steps 2 and 3 of Example 8 were repeated. The concentration of porcine somatotropin in the inclusion body suspension in the solubilizing process was 2.3 g/l.

The renaturation yield(%) of porcine somatotropin was about 90% based on the amount of somatotropin in WFIW-2 and overall purification yield was 28.5% based on the amount of somatotropin in Cell F.

While the invention has been described with respect to the above specific embodiments, it should be recognized that various modifications and changes may be made to the invention by those skilled in the art which also fall within the scope of the invention as defined by the appended claims.

What is claimed is:

1. A process for the preparation of biologically active somatotropin from inclusion bodies of a recombinant host cell containing an inactive form of said somatotropin protein, which comprises the steps of:

(a) contacting the inclusion bodies with an aqueous alcohol solution at an alkaline pH in the absence of a chaotropic agent to solubilize said protein; and (b) bringing the solubilized-protein into contact with a mild oxidizing agent to refold and form intramolecular disulfide bonds between cysteine residues of said protein.

2. The process of claim 1, wherein the alcohol is n-propyl alcohol or isopropyl alcohol.

3. The process of claim 2, wherein the concentration of isopropyl alcohol or n-propyl alcohol in step (a) ranges from 10 to 50%.

4. The process of claim 2, wherein the concentration of isopropyl alcohol or n-propyl alcohol in step (b) ranges from 10 to 35%.

5. The process of claim 2, wherein isopropyl alcohol or n-propyl alcohol is removed before step (b).

6. The process of claim 1, wherein the mild oxidizing agent is air.

7. The process of claim 1, wherein said recombinant host is *E. coli*.

8. The process of claim 1, wherein said somatotropin is mammalian, avian or fish somatotropin.

9. The process of claim 1, wherein said somatotropin is selected from the group consisting of human, bovine, porcine, horse, goat, ovine, canine, feline, chicken, flatfish, rockfish, salmon and eel somatotropin.

10. The process of claim 1, wherein said process is conducted at a temperature ranging from 0 to 500° C.

11. The process of claim 1, wherein step (a) is conducted at a pH above 9.

12. The process of claim 1 wherein step (b) is conducted at a pH above 8.4.

13. The process of claim 1 wherein the concentration of somatotropin in step (a) ranges from 1 to 10 g/2.

14. The process of claim 1, wherein a reducing agent is added to the aqueous solution in step (a).

15. The process of claim 14, wherein said reducing agent is selected from the group consisting of 2-mercaptoethanol, cysteamine, glutathione, cysteine or a redox mixtures thereof.

16. The process of claim 14, wherein said reducing agent is 2-mercaptoethanol used at a concentration ranging from 0.0001% to 0.5%.

17. The process of claim 1, wherein a reducing agent is added in step (b).

18. The process of claim 17, wherein said reducing agent is selected from the group consisting of 2-mercaptoethanol, cysteamine, glutathione, cysteine and redox mixtures thereof.

19. The process of claim 17, wherein said reducing agent is 2-mercaptoethanol used at a concentration ranging from 0% to 0.25%.

* * * * *